United States Patent [19]
Kawahara et al.

[11] Patent Number: 5,417,649
[45] Date of Patent: May 23, 1995

[54] FLUID TRANSFUSING DEVICE AND METHOD OF CONTROL THEREFOR

[75] Inventors: Masafumi Kawahara, Nara; Akihiro Maeda, Soraku, both of Japan

[73] Assignee: Sharp Kabushiki Kaisha, Osaka, Japan

[21] Appl. No.: 69,393

[22] Filed: Jun. 1, 1993

[30] Foreign Application Priority Data

Jun. 1, 1992 [JP] Japan .................. 4-140569

[51] Int. Cl.⁶ .............. A61M 37/00; F04B 41/06
[52] U.S. Cl. .................. 604/4; 128/DIG. 13; 364/510; 417/5; 417/8; 417/286; 417/290
[58] Field of Search .................. 604/4–6, 604/66, 67, 50–52, 246, 251–253; 128/DIG. 13; 364/510; 417/5, 7, 8, 12, 17, 62, 286, 289, 290, 426

[56] References Cited

U.S. PATENT DOCUMENTS

| | | | |
|---|---|---|---|
| 4,551,068 | 11/1985 | Boudreaux | 417/8 |
| 4,681,563 | 7/1987 | Deckert et al. | 604/67 |
| 4,756,706 | 7/1988 | Kerns et al. | 604/66 |
| 4,821,028 | 4/1989 | Deckert et al. | 128/DIG. 13 |
| 5,078,683 | 1/1992 | Sancoff et al. | 604/67 |
| 5,259,731 | 11/1993 | Dhinasa et al. | 417/7 |

FOREIGN PATENT DOCUMENTS 0047189 3/1983 Japan .................. 417/7

*Primary Examiner*—Randall L. Green
*Assistant Examiner*—Rob Clarke

[57] ABSTRACT

A fluid transfusing device and method of control therefor includes a plurality of pump driving portions and a microprocessor. Each pump driving portion is for driving a pump, and the microprocessor controls the pump driving portions. The microprocessor executes a fluid transfusing device control program, and interrupts the fluid transfusing device control program upon receiving a pump interrupt. The microprocessor then executes a pump driving interrupt module. When the microprocessor executes the pump driving module, the microprocessor generates a pump driving pulse to control a pump driving portion associated with the pump corresponding to the pump interrupt, determines receipt of another pump interrupt corresponding to a another pump, and generates a pump driving pulse to control a pump driving portion associated with the another pump corresponding to the another pump interrupt. Determining the receipt of another pump interrupt and generating another pump drive pulse without exiting the pump driving interrupt module, prevents undue delay in processing the another pump interrupt. Consequently, the pump drive portions, which are motors, do not disengage or stop due to delay in receiving pump drive pulses.

18 Claims, 6 Drawing Sheets

FLUID TRANSFUSING DEVICE AND METHOD OF CONTROL THEREFOR

BACKGROUND OF THE INVENTION

The present invention generally relates to a fluid transfusing device and a method of control therefor for injecting into a body.

A fluid transfusing pump to be used in the clinical examination at the hospital had only one pump driving portion per unit at the beginning of the development thereof. Medical fluids may be transfused with the use of as many as ten to fifteen fluid transfusing pumps per patient when the curing operation is effected with respect to patients of advanced diseases. In such a case, an electrocardiograph, a pulmotor, a clinical thermometer and so on had to be used at the same time with respect to the patient, thus making the small sick-room much narrower in space and the bed and its vicinity complicated. Activities by doctors and nurses engaged in curing operations were interfered with. Therefore, a transfusing pump with two pump driving portions or more provided in it has been developed so as to better use the sick-room.

A function of feeding the fluid while automatically switching an operation with a plurality of fluid transfusing patterns being stored, a function of storing transfused fluid accumulated values for each unit time with a clocking means, a function of storing the pump accumulated operation time so as to call out, many adding functions such as controlling operation and so on through communications by a computer are demanded, in addition to a basic function of a fluid transfusing pump for feeding the medical fluid. Thus, biger burdens are applied only upon one microprocessor (central processing unit). The details thereof will be described hereinafter.

The conventional fluid transfusing pump has one microprocessor control the plurality of pump driving portions even in the conventional fluid transfusing pump having a plurality of pump driving portions. This is because the motor driving pulses can be outputted without delay with respect to a plurality of pump driving portions especially without improvements in software as additional functions in the fluid transfusing pump are less and burdens demanded by the microprocessor are less.

In FIG. 4, the electrical construction of the conventional fluid transfusing pump having two pump driving portions is shown as a block diagram. The fluid transfusing pump is a positive pressure peristaltic type of vein injecting apparatus, and is used together with a fluid transfusing set. Two pump driving portions are provided, because two medical fluids, whose effects are different, are transfused at the same time at fluid feeding speeds different at the same time. This is satisfactory only when the fluids are fed correctly at a set speed with two independent pumps.

In FIG. 4, reference numerals 1a, 1b are first and second pump head portions, which apply fluid feeding force by the depressing pressure of a tube with a a straight line peristaltic type of fluid transfusing pump mechanism designed for fluid feeding set use. The pump head portions 1a, 1b are adapted to be driven by first and second stepping motors not shown. Reference numerals 2a, 2b are first and second motor driving circuits for driving the respective stepping motors with the motor driving pulses to be outputted from the microprocessor (central processing unit) 100. Reference numerals 3a, 3b are motor rotation detecting circuits for reporting to the microprocessor 100 each time the fluid feeding amount through the respective pump head portions 1a, 1b by the respective motor driving circuits 2a, 2b becomes a unit flow quantity in accordance with the detection of the rotation amount of the respective pump driving portions. Reference numerals 4a, 4b are first and second upper flow block detecting circuits for detecting the pressure reduction caused by abnormalities such as choking and so on of filters in the fluid feeding set between each medical fluid bag and the pump driving portion. When the transfusing pump is operated and a warning is issued from the upper flow block detecting circuits, the driving operation of the pump is adapted to be stopped. Reference numerals 5a, 5b are first and second lower flow choke detecting circuits for detecting the pressure rise caused by abnormalities such as choking and so on in the fluid transfusing tube between the respective pump driving portion and the patient. When the transferring pump is operated and a warning is issued by the lower flow block detecting circuits, the driving operation of the pump is adapted to be stopped. Reference numerals 6a, 6b are first and second air bubble detecting circuits for detecting the air bubbles caused, of regulated amount or more, within each fluid transfusing tube. When the transferring pump is operated and a warning is issued by the air bubble detecting circuits, the driving operation of the pump is stopped to prevent the air bubbles from going into blood vessels of the patient. Reference numerals 7a, 7b are first and second door open detecting circuits for detecting the open condition of the door for opening and, closing the pump driving portion when the fluid transfusion tube is set into the pump driving portion. When the door is unexpectedly opened during the driving operation of the pump driving portion, a warning is issued and, the driving operation of the pump is adapted to be stopped. Reference numerals 8a, 8b are first and second driving condition displaying portions for lamp-displaying the fluid transfusing operation, the non-operation and the warning about the pump driving portion. Reference numerals 9a, 9b are first and second warning displaying portions for displaying all the warning messages about the respective pump driving portions. Reference numerals 10a, 10b are first and second displaying portions for displaying all the information about the fluid transfusion such as fluid transfusion amount, predetermined fluid transfusion amount, accumulated fluid transfusion values and so on with respect to the respective pump driving portions.

Reference numeral 100 is a microprocessor (central processing unit) in charge of the controlling operation of the whole fluid transfusing pump and is provided with a counter, a register, and flags (FRC, OCR1, OCR2, OCRFLG) to be described later. Reference numeral 200 is a ROM (read only memory) where a program for operating the microprocessor 100 is accommodated.

Software for controlling the output of the motor driving pulses exists in the ROM200. Reference numeral 300 is a RAM (random access memory) where the fluid transfusion amount, the predetermined fluid transfusion amount key-inputted, the accumulated fluid transfusion values and the other types of data processed in operation by the microprocessor 100 are stored.

Reference numeral 11 is a key panel portion for key-inputting the various types of instructions. Numeric keys for inputting the fluid transfusion amount the predetermined fluid transfusion amount for setting the driving speed and time of the respective pump driving portions; a control key for supporting the inputs; a start key for starting the pump driving portion; a stop key for stopping the pump driving portion; a call key for displaying the accumulated fluid transfusion values and so on are provided on the key panel 11. Reference numeral 12 is a panel lock switch for making the inputs of the various types of keys prohibitive including the power key so that operations cannot be effected without permission. Reference numeral 13 is a power circuit for feeding the power to the respective circuit portions in the fluid transfusion pump. Reference numerals 14a, 14b are first and second power switches for turning on and off the power with respect to the first and second pump driving portions from the power circuit 13. Reference numeral 15 is a battery voltage detecting circuit for generating a warning, and, turning off the respective pump driving portion when the voltage of the storage battery is detected and becomes a given value or lower. The storage battery is charged by the power circuit 13 during the AC operation by the power circuit 13. Reference numeral 16 is a buzzer driving circuit for driving a warning sound generator when a warning condition has been judged. Reference numeral 17 is an A/D converting circuit converts voltage values into digital values for use by the microprocessor 100. The voltage values converted include the voltage values representing the currents flowing into the pump driving motor in the respective motor driving circuits 2a, 2b the detected voltage values from the respective air bubbles detecting circuits 6a, 6b, and the battery voltage values from the battery voltage detecting circuit 15.

A method of controlling two pump driving portions in the fluid transfusion pump will be described hereinafter.

The microprocessor 100 has the following counter and register. They are all composed of 16 bits.

FRC (Free Running Counter)
OCRI (Output Compare Register 1)
OCR2 (Output Compare Register 2)

The time counter FRC is a counter for automatically effecting an up count (increment) for each 500 nsec by the internal function of the microprocessor 100 independently from the execution of the software controlling the microprocessor 100. The time counter FRC starts from "0" and increases to "FFFF" (hexadecimal representation) a resetting operation is effected after the outputting of FFFF so as to return to "0" again. The OCR1 is a register for a first pump driving portion use. The OCR2 is a register for a second pump driving portion use. Both the resisters OCR1, OCR2 are adapted to write or read independently with each other the values from the "0" to "FFFF". Comparative reference values for timing control use the outputs of the motor driving pulses with respect to the first and second pump driving portions these values are inputted respectively to both the registers OCR1, OCR2.

Two output compare interrupts
OCI1 (Output Compare Interrupt 1)
OCI2 (Output Compare Interrupt 2) are adapted to be generated as the interrupt function of the software.

A first interrupt OCI1 is generated when the count value by the time counter FRC has conformed to the content (comparative reference value) of the first register OCR1 (FRC=OCR1). A second interrupt OCI2 is generated when the count value by the time counter FRC has conformed to the content (comparative reference value) of the second register OCR2 (FRC=OCR2). The comparative reference value of the first register OCR1 and the comparative reference value of the second register OCR2 are handled independently with respect to each other. Accordingly, although the generation of the first interrupt OCI1 and the generation of the second interrupt OCI2 are independent with respect to each other, the execution address (subroutine) on the software to be executed after the interrupt generation becomes common. The common execution location (execution module) is represented as the interrupt OCI.

It is necessary to tell whether the cause exists in a first interrupt OCI1 or in a second interrupt OCI2 in the execution of the common interrupt OCI.

An 8-bit flag OCRFLG to be set by the internal function of the microprocessor 100 is prepared. It is adapted to be recognized by a first interrupt OCI1 when a first bit of the flag OCRFLG is set to "1". It is adapted to be recognized by a second interrupt OCI2 when a second bit of the flag OCRFLG is set to the "1". Although each bit of the flag OCRELG can reset to "0" by the software, it cannot be set to the "1". The bit can be set to the "1" by the microprocessor 100 only when first or second interrupts OCI1, OCI2 have generated. As the first interrupt OCI1 and the second interrupt OCI2 can be generated independently, the first and second bits of the flag OCRFLG can be also made "1" at the same time.

A method of outputting the motor driving pulses for concrete motor controlling operation will be described in a first pump driving portion.

Assume that the time interval value of the motor driving pulse is d. Assume that the count value of the time counter FRC is, for example, $FRC = f_0$ in the timing of the driving start of the pump. The output timing of a first motor driving pulse is $FRC = f_0 + d$ The content of the first register OCR1 is set to put $OCR1 = f_0 + d$ the first interrupt OCI1 in a generable condition. When the time has become $(f_0 \div d)$, the count value of the time counter FRC becomes as follows, $FRC = f_0 + d$ $FRC = OCR1$ a first interrupt OCI1 is generated and a first motor driving pulse is outputted.

Assume that $f_1 = f_0 + d$ and the content of a first register OCR1 is set $OCR1 = f_1 + d$ a second motor driving pulse is outputted in the time $(f_1 \div d = f_0 + 2d)$. The microprocessor 100 effects the processing operation except for the pump driving operation within the time d from a certain interrupt OCI1 to the next interrupt OCI1.

In the past, two pump driving portions were controlled with such a flow chart shown in FIG. 5 by the use of such specification of microprocessor 100 as described hereinabove. A controlling operation will be described concretely hereinafter.

When a count value of a time counter FRC conforms to the content of first or second register OCR1, OCR2 so as to generate the interrupt OCI, the microprocessor 100 temporarily interrupts the program during the execution at present so as to start the execution of the interrupt OCI processing module. At a step n1, it is judged whether or not a first bit of a flag OCRFLG is set to "1", namely, the interrupt OCI depends upon a first interrupt OCI1. When the judgment is affirmative, the step goes to a step n2 so as to reset to the "0" the first bit of the flag OCRFLG. Then, at a step n3, a motor driving pulse is outputted with respect to a first motor driving circuit 2a for driving a first pump driving portion. At a step n4, a value to become, next, a time counter FRC=OCR1 is obtained by the calculation as preparation for generating the next first interrupt OCI1 so as to set the calculation result in the first register OCR1. Then, the step returns to the interrupt address so as to resume the temporarily interrupted program.

When a first bit of the flag OCRFLG becomes "0" in the judgment of the step n1, it is judged that the interrupt OCI is not due to the first interrupt OCI1. The step advances to a step n5 to judge whether or not a second bit of the flag OCRFLg is set to "1" so as to confirm that it is due to a second interrupt OCI2. When the judgment is affirmative, the step advances to a step n6 to reset the second bit of the flag OCRFLG into "0". Then, at a step n7, a motor driving pulse is outputted with respect to a second motor driving circuit 2b for driving the second pump driving portion. At a step n8, a value to become, next, a time counter FRC=OCR2 is obtained as preparation for generating the next second interrupt OCI2 so as to set the calculation result in the second register OCR2. Then, the step returns to the interrupt address so as to resume the temporarily interrupted program.

When the judgment of the step n5 is negative, it follows that the interrupt OCI has been generated although both the first interrupt OCI1 and the second interrupt OCI2 are not the cause. It is considered to be caused due to some disturbance. A proper error processing operation has only to be effected. The step is to return only to the address of the interrupt destination.

A problem in the conventional embodiment will be described hereinafter with the use of a timing chart of FIGS. 6(a)–6(d). FIG. 6 (a) shows a motor driving pulse when a stepping motor is caused to rotate with a driving method of 1-2 phase excitation. Four coils of A, B, C, D are provided in the motor. Eight coil excitement patterns from (1) to (8) are caused in order with the execution timing of a first interrupt OCI1 (or second interrupt OCI2) so as to cause the motor to rotate. Reference character d is the execution interval of an interrupt OCI1 (OCI2). The output of the motor driving pulse is to generate the excitation patterns. The patterns in the respective periods (1) through (8) are as follows. Reference numeral 1 shows an excited condition, and reference numeral 0 shows a non-excited condition.

|     | A | B | C | D |
|-----|---|---|---|---|
| (1) | 1 | 0 | 0 | 1 |
| (2) | 1 | 0 | 0 | 0 |
| (3) | 1 | 1 | 0 | 0 |
| (4) | 0 | 1 | 0 | 0 |
| (5) | 0 | 1 | 1 | 0 |
| (6) | 0 | 0 | 1 | 0 |
| (7) | 0 | 0 | 1 | 1 |
| (8) | 0 | 0 | 0 | 1 |

As shown in FIG. 6 (a), the stepping motor is caused to rotate by the phase change of the excitation with respect to four coils A, B, C, D of the stepping motor in the time interval value d of the motor driving pulse. It is originally desired that the composite magnetic field by four coils not be changed across the interval of time d. The delay time $t_0$ does not matter when it is short as in FIG. 6 (b) if the time delay by the interrupt processing operation except for the driving operation of the motor is caused. As the additional function of the fluid transfusing pump is increased as described hereinabove, the interrupt processing operation except for the driving operation of the motor increases so that the time delay becomes the time $t_e$ of the length which cannot be tolerated as in FIG. 6(c). At such a time, sufficient excitation time necessary for the rotation thereof is not given with respect to the stepping motor, thus resulting in disengaged motor condition. In the worst condition, the motor may be stopped.

The concrete example will be described. There are, for example, a sensor data sample demand (Int1) for upper/lower flow choke detection, a sensor data sample demand (Int2) for air bubble detection and a power voltage sample demand (Int3) as an interrupt processing operation the software has to execute except for the motor driving operation. Assume that a delaying operation is effected 500 nsec by 500 nsec which is an execution cycle time of the microprocessor 100 in a certain timing and an interrupt demand is caused in the order of the OCI1, the int1, int2 the Int3, the OCI2. The execution time of the respective modules is as follows.

| OCI1 | 100 μsec |
| Int1 | 30 μsec |
| Int2 | 30 μsec |
| Int3 | 30 μsec |
| OCI2 | 100 μsec |

A motor is required to be rotated so that the time interval value d becomes d=450 μsec when the fluid transfusing pump is operated at the highest speed (fluid transfusing speed 1999 ml/hr).

In order to cause the motor to rotate without disengagement thereof, the delay time $t_e$ to be tolerated becomes as follows $t_e$=d/3=150 μsec because it can be ensured experimentally that the time delay till the d/3 is tolerated with respect to the ideal time interval value d. In the above described embodiment, the time delay of 100+30+30+30 =190 (μsec)

is caused (see FIG. 6(d)) with respect to the second interrupt OCI2 in the above described embodiment. As it exceeds the maximum delay time $t_e$ (=150 μsec) to be tolerated, the rotation with respect to the second interrupt OCI2 cannot be guaranteed. Namely, the disengagement of the motor may cause it to stop. The multiple functions interfere with the pump driving operation which is the original function of the fluid transfusing pump. A possibility of causing such a problem can not be allowed by any means in the fluid transfusing pump as medical curing apparatuses which have influences upon human lives.

As one measure for solving it, it is considered to increase the number of microprocessors to reduce the burdens of the microprocessor. Increased cost per fluid transfusing pump is caused and data communication for the operation control among the microprocessors is required. Accordingly, the solving measures are not realistic. As another measure, it is considered to use a faster microprocessor. The microprocessor however is of higher cost, and the respective circuit portions of the fluid transfusing pump are required to be designed again in accordance with the higher speed microprocessor. Therefore, more time is taken for the development, and stupendous investments are required.

SUMMARY OF THE INVENTION

Accordingly, the present invention has been developed with a view to substantially eliminate the above discussed drawbacks inherent in the prior art, and to provide an improved fluid transfusing device and method of control therefor.

Another important object of the present invention is to provide an improved fluid transfusing device which can normally operate multiple functions of fluid transfusing device, without causing the disengagement and/or stop of the motor, having a plurality of pump driving portions with the use of one microprocessor having the same functions as discussed above. A fluid transfusing device and method of control therefor of the present invention includes a plurality of pump driving portions and a microprocessor. Each pump driving portion is for driving a pump, and the microprocessor controls the pump driving portions. The microprocessor executes a fluid transfusing device control program, and interrupts the fluid transfusing device control program upon receiving a pump interrupt. The microprocessor then executes a pump driving interrupt module. When the microprocessor executes the pump driving module, the microprocessor generates a pump driving pulse to control a pump driving portion associated with the pump corresponding to the pump interrupt, determines receipt of another pump interrupt corresponding to a another pump, and generates a pump driving pulse to control a pump driving portion associated with the another pump corresponding to the another pump interrupt. Determining the receipt of another pump interrupt and generating another pump drive pulse without exiting the pump driving interrupt module, prevents undue delay in processing the another pump interrupt. Consequently, the pump drive portions, which are motors, do not disengage or stop due to delay in receiving pump drive pulses.

These and other objects of the present invention will become more readily apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE INVENTION

Figure 1:
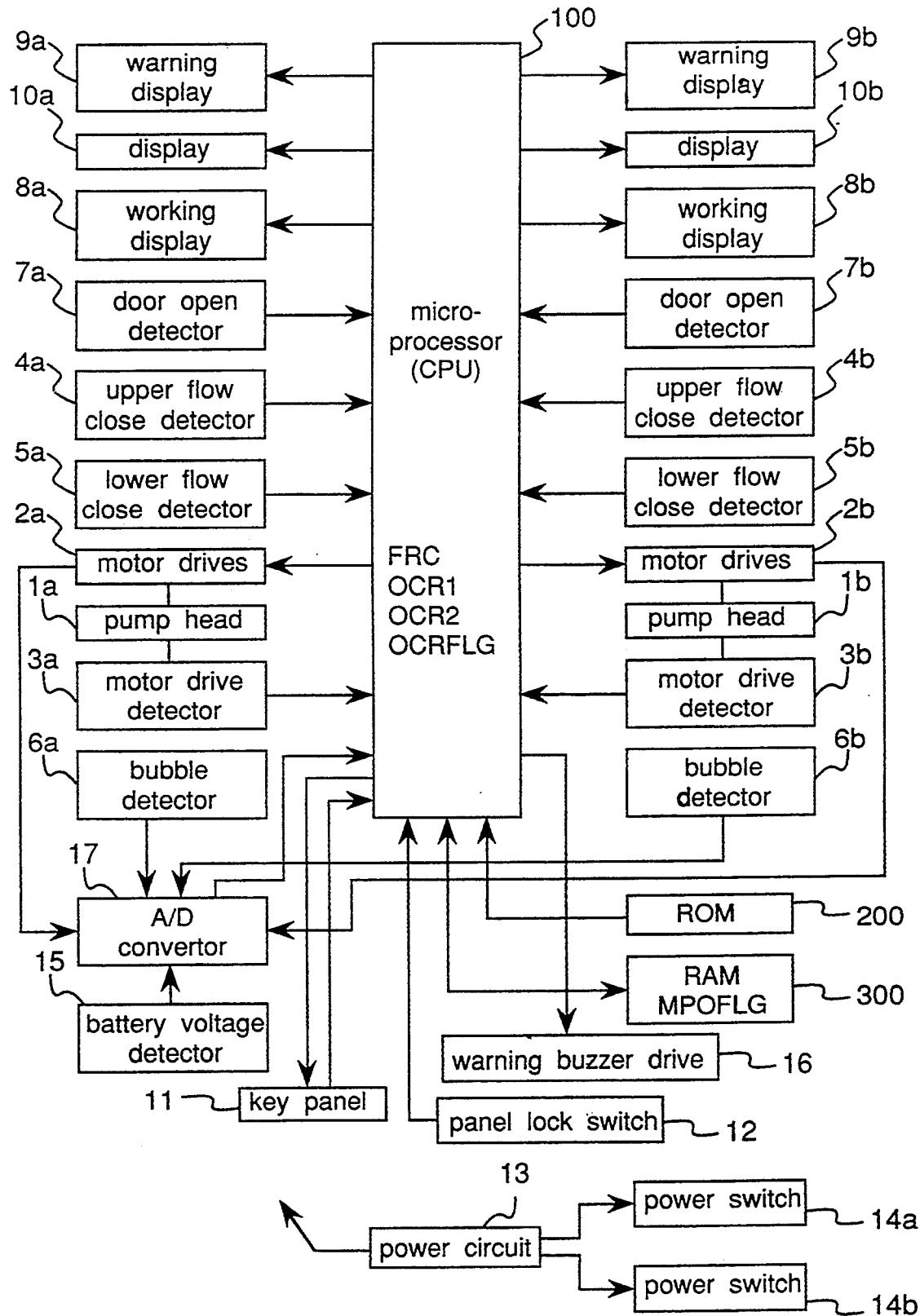
FIG. 1 is a block diagram showing the electric construction of a fluid transfusing pump in accordance with one embodiment of the present invention.

Before the description of the present invention proceeds, it is to be noted that like parts are designated by like reference numerals throughout the accompanying drawings.

One embodiment of a fluid transfusing device in accordance with the present invention will be described hereinafter with reference to the drawings.

Figure 4:
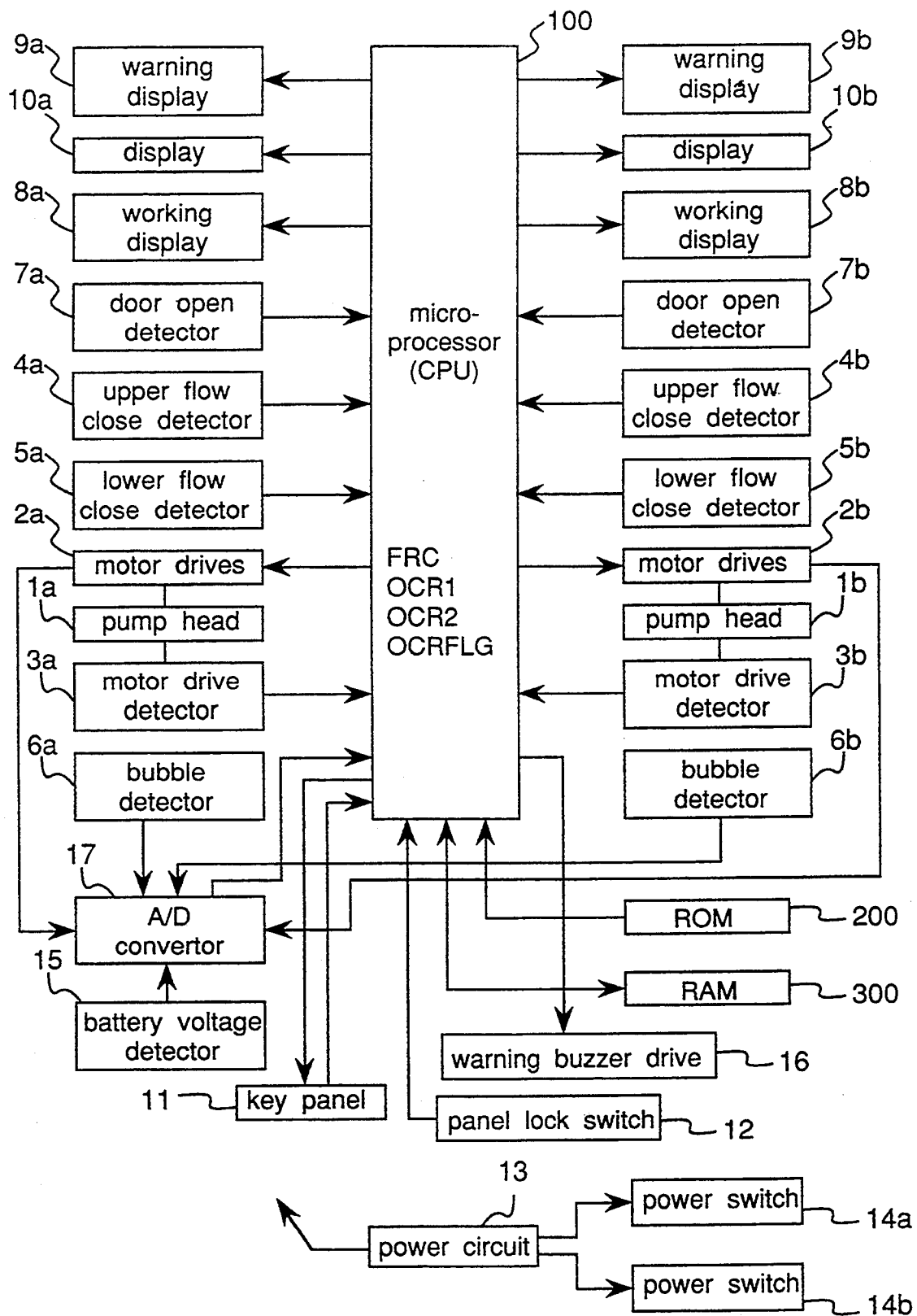
FIG. 4 is a block diagram showing the electrical construction of a fluid transfusing pump in accordance with the conventional embodiment.
Figure 5:
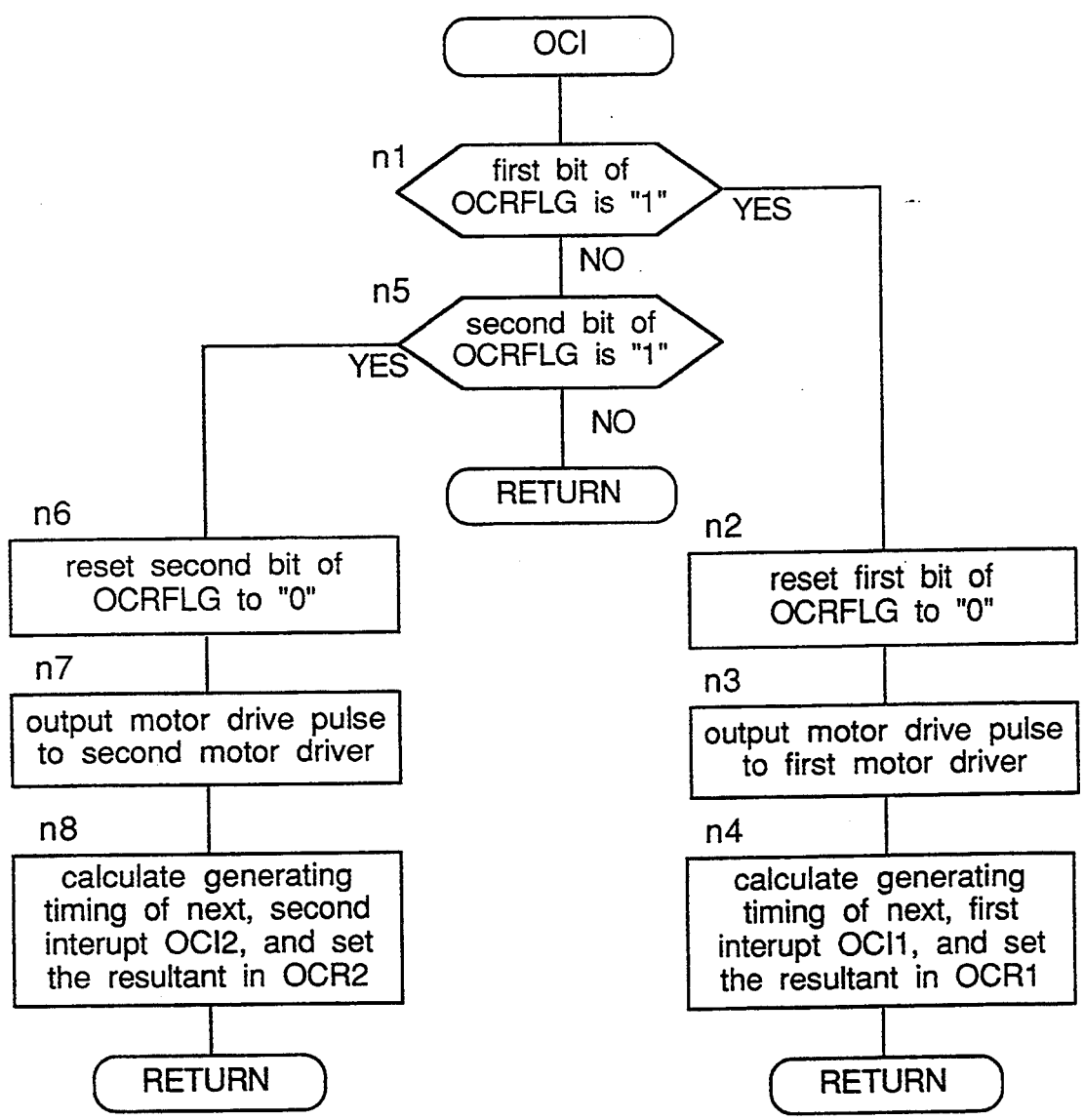
FIG. 5 is a flow chart to be used for the operation description in the conventional embodiment.
Figure 6A:
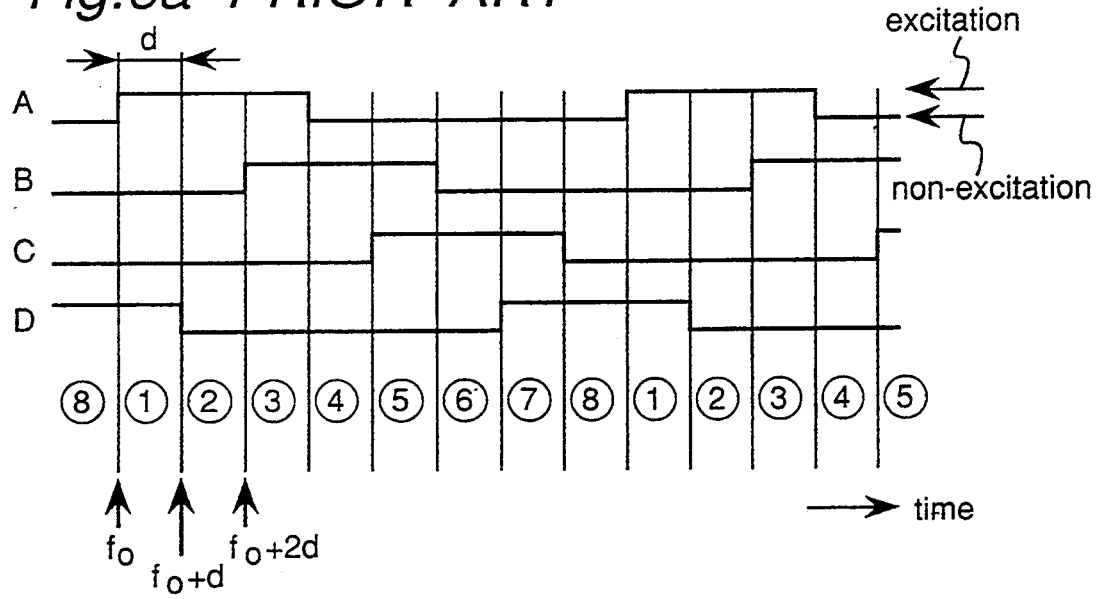
FIG. 6(a) illustrates motor driving pulses in the conventional embodiment.
Figure 6B:
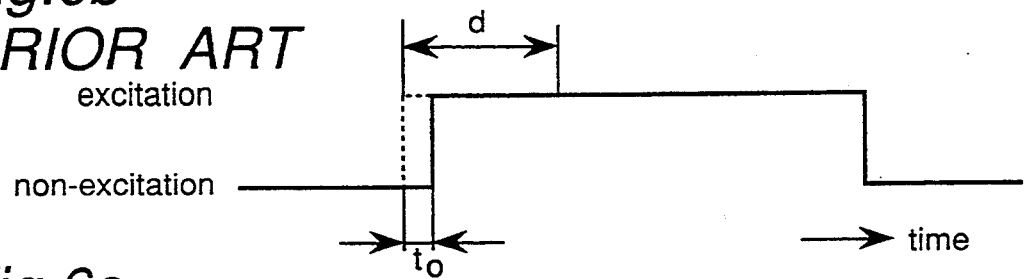
FIG. 6(b) is a timing chart to illustrate the operation of the conventional embodiment and the problems associated therewith.
Figure 6C:
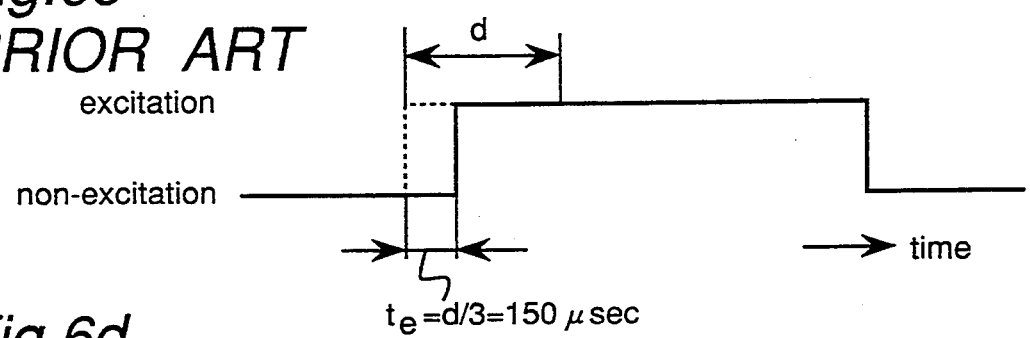
FIG. 6(c) is a timing chart to illustrate the operation of the conventional embodiment and the problems associated therewith.
Figure 6D:
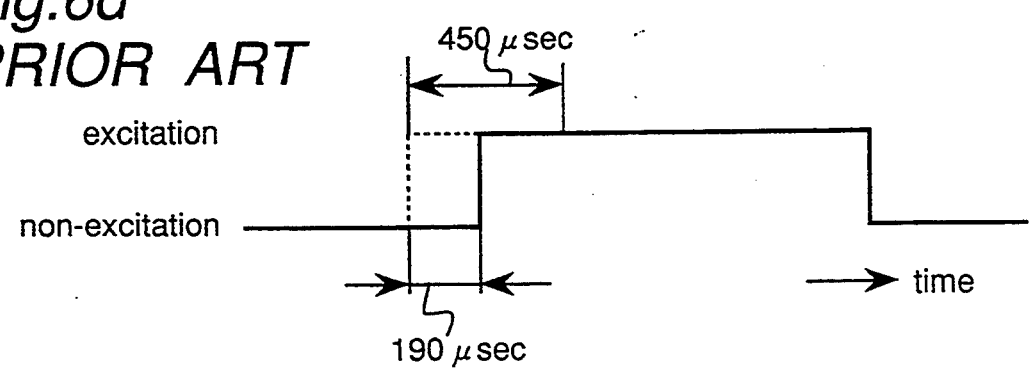
FIG. 6(d) is a timing chart to illustrate the operation of the conventional embodiment and the problems associated therewith.

FIG. 1 is a block diagram showing the electrical construction of an embodiment of a fluid transfusing device (vein injecting apparatus of a positive pressure peristaltic type). In FIG. 1, the same reference characters as in FIG. 4 in the conventional embodiment show the same components or the same portions even in the present embodiment. Namely, reference characters 1a, 1b are pump head portions. Reference numerals 2a, 2b are motor driving circuits. Reference numerals 3a, 3b are motor rotation detecting circuits. Reference numerals 4a, 4b are upper flow choke detecting circuits. Reference characters 5a, 5b are lower flow choke detecting circuits. Reference characters 6a, 6b are air bubble detecting circuits. Reference characters 7a, 7b are door open detecting circuits. Reference characters 8a, 8b are operation condition displaying portions. Reference characters 9a, 9b are warning displaying portions. Reference characters 10a, 10b are displaying portions, reference numeral 11 is a key panel portion, reference numeral 12 is a panel lock switch, reference numeral 13 is a power circuit, reference characters 14a, 14b are power switches, reference numeral is a battery voltage detecting circuit, reference numeral 16 is a buzzer driving circuit for warning sound use, reference numeral 17 is an A/D converting circuit, reference numeral 100 is a microprocessor, reference numeral 200 is a ROM, reference numeral 300 is a RAM.

The different points, different from the conventional embodiment, in the present embodiment are that a flag MPOFLG which means the completion of the output of the motor driving pulse in the RAM300 has been added. The motor driving pulse output completion flag MPOFLG is 8 bits. The motor driving pulse output completion flag MPOFLG firstly shows that the calculation of the timing of the next first interrupt OCI1 is not effected yet although the output of the motor driving pulse with respect to the first motor driving circuit 2a has been competed when a first bit is set to "1". The motor driving pulse output completion flag MPOFLG secondly shows that the calculation of the timing of the next second interrupt OCI2 is not effected yet although the output of the motor driving pulse with respect to the second motor driving circuit 2b has been completed when a second bit is set to "1".

The other construction is similar to that of the conventional embodiment except for a point that the form of the motor driving pulse output is provided in accordance with the present embodiment in a program accommodated in the ROM 200.

Figure 2:
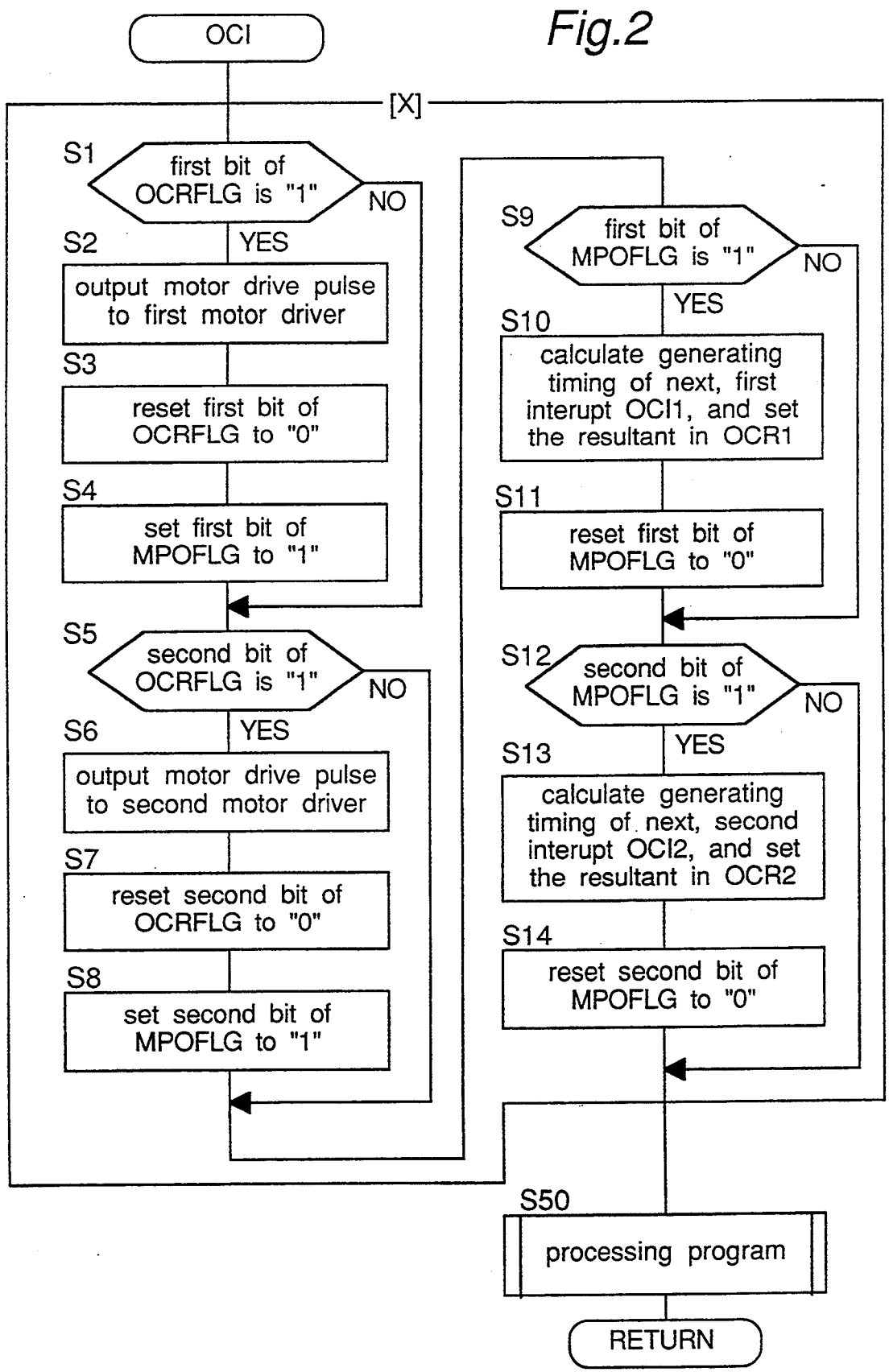
FIG. 2 is a flow chart to be used for the operation description of the embodiment.

The operation of the fluid transfusing device in the present invention will be described in accordance with the flow chart of FIG. 2. The counters, registers, and flags of the conventional embodiment are to be used. In the microprocessor 100,

| FRC | (Free Running Counter) |
|---|---|
| OCR1 | (Output Compare Register 1) |
| OCR2 | (Output Compare Register 2) |
| OCRFLG | (first bit = 1: first interrupt OCI1 second bit = 1: second interrupt OCI2) | are provided. As the motor driving pulse output completion flag newly added in the present embodiment, there is provided

| MPOFLG | (first bit = 1: first motor driving pulse output completion second bit = 1: second motor driving pulse output completion) |
|---|---|

When the count value of the time counter FRC conforms to the contents of the first or second register OCR1, OCR2 so as to generate an interrupt OCI, the microprocessor 100 temporarily interrupts the program to be executed at present so as to start the execution of the common interrupt OCI processing module. As the first interrupt OCI1 and the second interrupt OCI2 are generated independently, it is judged whether or not the first bit of the flag OCRFLG is set to "1" at the step S1, namely, whether or not the interrupt OCI depends upon a first interrupt OCI1 for discrimination between the first interrupt OCI1 and the second interrupt OCI2.

When the judgment is affirmative, a step advances to a step S2, and the motor driving pulse is outputted with respect to the first motor driving circuit 2a for driving the first pump driving portion. At a step S3, a first bit of the flag OCRFLG is reset into "0" for permission of the next first interrupt OCI1. Although a motor driving pulse is outputted with respect to the first motor driving circuit 2a, at the step S4, a first bit of the motor driving pulse output completion flag MPOFLG is set into "1" so as to show that the calculation of the timing of the next first interrupt OCI1 is not effected yet.

Continuously, the step advances to the step S5 so as to judge whether or not the second bit of the flag OCRFLG is set to "1", namely whether the demand of the second interrupt OCI2 is made. When the judgment becomes affirmative, the step advances to the step S6 so as to output the motor driving pulse with respect to the second motor driving circuit 2b so as to drive the second pump driving portion during the execution of the module of the processing of the interrupt OCI.

Conventionally the returning operation was effected to the address of the interrupting destination so as to resume the temporarily interrupted program after the outputting of the motor driving pulse to the first motor driving circuit 2a so as to judge whether or not the motor driving pulse should be outputted to the second motor driving circuit 2b. Therefore, the processing could move to the interrupt processing except for the pump driving portion, thus causing the delay in the output of the motor driving pulse with respect to the second motor driving circuit 2b. In the case of the present embodiment, it is judged whether or not the motor driving pulse should be outputted immediately to the second motor driving circuit 2b without the returning operation to the interrupting destination. The motor driving pulse is adapted to be outputted when the outputting operation should be effected. The other interrupts are prohibited so that the output day as before can be avoided.

The second bit of the flag OCRFLG is reset into so as to permit the next second interrupt OCI2 at the step S7 after the motor driving pulse has been outputted to the second motor driving circuit 2b at the step S6 in this manner. At the step S8, the motor driving pulse was outputted with respect to the second motor driving circuit 2b. The second bit of the motor driving pulse output completion flag MPOFLG is set to the "1" so as to show that the calculation of the next second interrupt OCI2 is not effected yet.

The step skips to a step S5 when the judgment of the step S1 becomes negative. The step skips to a step S9 when the judgment of the step S5 becomes negative.

It is judged at a step S9 whether or not the first bit of the motor driving pulse output completion flag MPOFLG is "1". That the first bit of the motor driving pulse output completion flag MPOFLG becomes "1" means that the calculation is not effected yet about the timing for generating the next first interrupt OCI1 although the motor driving pulse is outputted with respect to the first motor driving circuit 2a at the step S2. The step advances to a step S10 so as to obtain by calculation, next, a value to become a time counter FRC=OCR1 as preparation for generating the next first interrupt OCI1 for setting the calculation result in the first register OCR1. The calculating method is similar to the conventional one. The first interrupt OCI1 at this time is FRC=OCR1=$f_0$ as a count value of the time counter FRC with the time interval value of the motor driving pulse being d, the timing of the next first interrupt OCI1 has to become $f_1 = f_0 + d$ so that OCR1=$f_0+d$ is to set. The step advances to a step S11 to complete the calculation so that a first bit of the motor driving pulse output completion flag MPOFLG is reset into "0".

At a step S12, it is judged whether or not a second bit of the motor driving pulse output completion flag MPOFLG becomes "1". This means that the timing for generating the next second interrupt OCI2 is not calculated yet although the motor driving pulse is outputted with respect to the second motor driving circuit 2b at a step S6. The step advances to a step S13 so as to obtain by calculation, next, a value to become a time counter FRC=OCR2 as preparation for generating the next second interrupt OCI2 to set the calculation result in the second register OCR2. As the step advances to a step S14 to complete the calculation, a second bit of the motor driving pulse output completion flag MPOFLG is reset into "0".

When the judgment of the step S9 becomes negative, the step skips to a S12. When the judgment of the step S12 becomes negative, the step skips to a step S50.

When a processing program from the above described step S1 to a step S14 is [X], the subroutine of the step S50 is to execute again the processing program [X]. The returning operation is effected to an address of the interruption destination at first from the completion of the execution of a second processing program [X]. The reason why the processing program [X] is executed twice, continuously is described below.

When the judgment at the step S1 is negative, and the judgment at the step S5 is affirmative, the motor driving pulse is not outputted to the first motor driving circuit 2a, the motor driving pulse is outputted only to the second motor driving circuit 2b. In the flag OCRFLG, the first bit is "0" and the second bit is "1". During the period from the step S5 to the step S14, the output demand of the motor driving pulse with respect to the first motor driving circuit 2a may be generated with a time counter FRC=OCR1. When the returning operation is effected to the address of the interruption destination without execution of the processing program [X] of the step S50 an unacceptable delay with respect to the first interrupt OCI1 can occur. In order to avoid such an inconvenience, the processing program [X] is executed twice on the OCI module. The motor driving pulse can be outputted without delay equally to each other even in the first interrupt OCI1 and even in the second interrupt OCI2.

Figure 3:
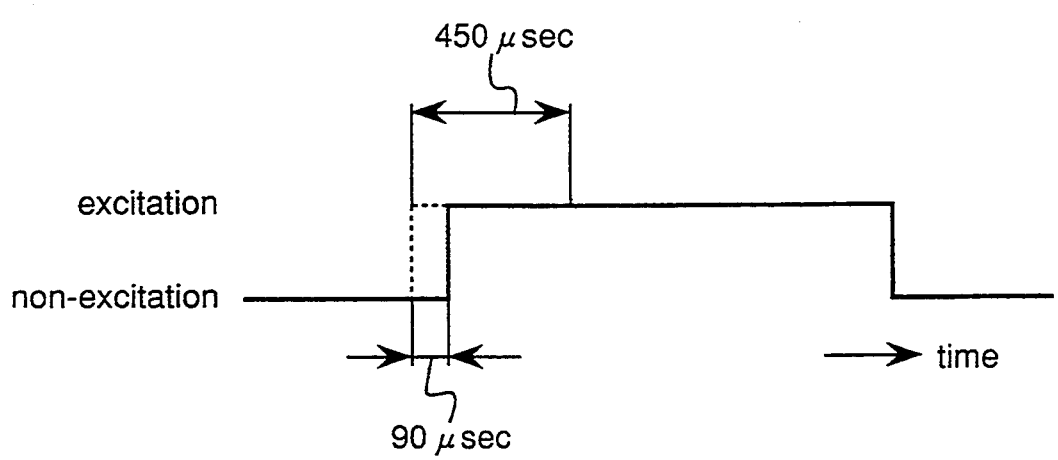
FIG. 3 is a wave form view showing the time delay in the motor diving interrupt processing operation in the embodiment.

As the above described result, both the output of the motor driving pulse in the first interrupt OCI! and the output of the motor driving pulse in the second interrupt OCI2 can be effected during the execution of one portion of the module of the interrupt OCI can be effected. As shown in the chart of FIG. 3, 30+30+30=90 ($\mu$sec) which are the total of the execution time of the sensor data sample demand (Int1) for upper flow/lower flow choke detecting operation, a sensor data sample demand (Int2) for the air bubble detection, and a power voltage sample demand (Int3) can be provided within the maximum tolerant delay time 150 $\mu$sec which does not cause the disengagement. Thus, the disengagement of the stepping motor can be avoided.

The processing delay to be caused by the execution time of OCI1, OCI2 which are required to drive two motors is hardly required to be taken into consideration. Only the delay of the interrupt processing except for the motor driving operation has only to be considered as the delay time to the motor. The designing operation has only to be effected so that the total of the interrupt processing time except for the motor driving operation may not cause the motor disengagement.

As is clear from the foregoing description, according to the arrangement of the present invention, the respective portions of the fluid transfusing pump provided with a plurality of pump driving operations, and multifunctioned can be controlled only with one microprocessor which is not made especially higher in speed, and a plurality of pump driving portions can be operated normally without causing the disengagement/stop of the motor.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as included therein.

What is claimed is:

1. A fluid transfusing device comprising:
    a plurality of pump driving portions, each pump driving portion for driving a pump;
    a processor controlling said pump driving portions, said processor
        (a) executing a fluid transfusing device control program;
        (b) interrupting said fluid transfusing device control program upon receiving a pump interrupt; and
        (c) executing a pump driving interrupt module, which includes,
            (c1) generating a pump driving pulse to control a pump driving portion associated with said pump corresponding to said pump interrupt,
            (c2) determining receipt of another pump interrupt corresponding to a another pump, and
            (c3) generating a pump driving pulse to control another pump driving portion associated with said another pump corresponding to said another pump interrupt.

2. The device of claim 1, wherein said processor further includes determining to which pump said pump interrupt corresponds prior to said (c1) generating a pump driving pulse.

3. The device of claim 1, wherein said processor includes
    a timer counting a time value;
    an interrupt reference memory storing a reference time value corresponding to each pump; and wherein said processor
        (d) compares said time value to said reference time values stored in said interrupt reference memory,
        (e) sets a pump interrupt flag corresponding to a pump which output of said (d) comparison indicates has a reference time value equal to said time value, and
        (f) generates a pump interrupt when output of said (d) comparison indicates that at least one of said reference time values equals said time value.

4. The device of claim 3, wherein said processor, prior to said (c1) generating, determines to which pump, and thus said pump driving portion, said pump interrupt corresponds based on said pump interrupt flags.

5. The device of claim 4, wherein said processor, in said (c2) determining, determines whether another pump interrupt flag is set.

6. The device of claim 5, wherein said processor, in said (c2) determining, stops execution of said pump driving interrupt module if no pump interrupt flags are set.

7. The device of claim 3, wherein said processor, after said (c1) generating, resets said pump interrupt flag corresponding to said pump driving portion receiving said pump driving pulse generated in said (c1) generating.

8. The device of claim 1, wherein said processor, in said (c) executing said pump driving interrupt module,
(c4) sets, after said (c1) generating, a status flag corresponding to said pump driving portion receiving said generated pump driving pulse;
(c5) calculating, after said (c2) determining, a new reference time value corresponding to said set status flag; and
(c6) storing said new reference time value in said interrupt reference memory.

9. The device of claim 1, wherein said processor interrupts execution of said fluid transfusing device control program upon receiving one of an sensor data sample demand interrupt for an upper and lower flow choke circuit, a sensor data sample demand interrupt for an air bubble detection sensor, and a power voltage sample demand interrupt for a power voltage sensor.

10. A method of controlling a fluid transfusing device having a plurality of pump driving portions, said method comprising the steps of:
(a) executing, in a processor, a fluid transfusing device control program;
(b) interrupting said fluid transfusing device control program upon receiving a pump interrupt; and
(c) executing, in said processor, a pump driving interrupt module, said step (c) including the steps of,
(c1) generating a pump driving pulse to control a pump driving portion associated with said pump corresponding to said pump interrupt,
(c2) determining receipt of another pump interrupt corresponding to a another pump, and
(c3) generating a pump driving pulse to control another pump driving portion associated with said another pump corresponding to said another pump interrupt.

11. The method of claim 10, wherein said step (c) further includes prior to step (c1) the step of (c0) determining to which pump said pump interrupt corresponds.

12. The method of claim 10, further comprising the steps of:
(d) counting with a counter a time value;
(e) storing, in an interrupt reference memory, a reference time value corresponding to each pump;
(f) comparing said time value to said reference time values stored in said interrupt reference memory;
(g) setting a pump interrupt flag corresponding to a pump which output of said step (f) indicates has a reference time value equal to said time value; and
(h) generating a pump interrupt when output of said step (f) indicates that at least one of said reference time values equals said time value.

13. The method of claim 12, wherein said step (c) includes the step, prior to said step (c1), of (c0) determining to which pump, and thus said pump driving portion, said pump interrupt corresponds based on said pump interrupt flags.

14. The method of claim 12, wherein said step (c) includes the step, after said step (c1), of resetting said pump interrupt flag corresponding to said pump driving portion receiving said pump driving pulse generated in said step (c1).

15. The method of claim 13, wherein said step (c2) includes the step of (c21) determining whether another pump interrupt flag is set.

16. The method of claim 15, wherein said step (c2) further includes the step of (c22) exiting said pump driving interrupt module if no pump interrupt flags are set.

17. The method of claim 10, wherein said step (c) further comprises the steps of:
(c4) setting, after said step (c1), a status flag corresponding to said pump driving portion receiving said pump driving pulse generated in step (c1);
(c5) calculating, after said step (c2), a new reference time value corresponding to said set status flag; and
(c6) storing said new reference time value in said interrupt reference memory.

18. The method of claim 10, further comprising the step of (d) interrupting execution of said fluid transfusing device control program upon receiving one of an sensor data sample demand interrupt for an upper and lower flow choke circuit, a sensor data sample demand interrupt for an air bubble detection sensor, and a power voltage sample demand interrupt for a power voltage sensor.

* * * * *